(12) United States Patent
Busch

(10) Patent No.: US 6,558,322 B1
(45) Date of Patent: May 6, 2003

(54) METHOD TO DETERMINE OLFACTORY PERCEPTION

(75) Inventor: Barbara Busch, Frankfurt (DE)

(73) Assignee: Analysis Research AG, Zug (CH)

( * ) Notice: Subject to any disclaimer, the term of this patent is extended or adjusted under 35 U.S.C. 154(b) by 0 days.

(21) Appl. No.: 09/539,679

(22) Filed: Mar. 30, 2000

(30) Foreign Application Priority Data

May 26, 1999 (DE) .......................................... 199 24 065

(51) Int. Cl.$^7$ ................................................. A61B 5/08
(52) U.S. Cl. ..................................... 600/303; 73/23.34
(58) Field of Search ....................... 600/303; 73/23.34

(56) References Cited

U.S. PATENT DOCUMENTS

| | | | |
|---|---|---|---|
| 4,265,248 A | 5/1981 | Chuiton et al. .............. | 128/630 |
| 4,411,156 A | 10/1983 | Lowe .......................... | 73/432 |
| 4,563,893 A | 1/1986 | Tanyolac et al. ............... | 73/23 |
| 4,934,386 A | 6/1990 | Walker et al. ............... | 131/329 |
| 5,380,765 A | 1/1995 | Hirsch ........................ | 514/731 |
| 5,457,983 A | 10/1995 | Sauvageau et al. .............. | 73/1 |
| 5,492,934 A | * 2/1996 | Hirsch ........................ | 514/730 |
| 5,562,740 A | * 10/1996 | Cook et al. .................. | 514/730 |
| 5,767,385 A | 6/1998 | Bundy et al. ............. | 73/23.34 |
| 6,006,583 A | 12/1999 | Hayashi ..................... | 73/23.34 |

OTHER PUBLICATIONS

Hummel et al, "'Sniffin Sticks':olfactory performance assessed by the combined testing of odor identification, odor discrimination, and olfactory threshold," Chemical Senses, Feb. 1997, 22(1), pp 39–52.*

Doty et al, "Development of the University of Pennsylvania Smell Identification test:. a standardized microencapsulated test of olfactory function," Physiology and behavior, vol. 32, pp. 489–502, 1984.*

Cain, "Testing olfaction in a clinical setting," Ear, Nose, and Throat Journal, Apr. 1989, vol. 68, pp. 322–328.*

McMahon et al, "Le Nez du Vin: A quick test of olfaction," Clinical Otolaryngology, vol. 21, pp. 278–280,, 1996.*

Kobal et al, "Sniffin Sticks: screening olfactory performance," Rhinology 34(4), Dec. 1996, pp. 222–226.*

Richman et al, "Assessment of an abbreviated odorant identification task for children,: a rapid screening device for schools and clinics," ACTA Pediatrics, 84(4) Apr. 1995, pp. 434–437.*

Nordin et al, "The Scandinavian Odor–Identificationb Test: development, repliability, validity, and normative data," ACTA Otolaryngology, 118(2) Mar. 1998, pp. 226–234.*

Wright, "Characterization of Olfactory dysfunction," Archives of Otolaryngology, Head, Neck surgery, 113(2) Feb. 1987, pp. 163–168.*

Kobal et al, "A combined psychophysical and electrophysical olfaction test," Chemical Senses, 17(6) 1992, pp. 850–851.*

* cited by examiner

Primary Examiner—Robert L. Nasser
(74) Attorney, Agent, or Firm—Milde & Hoffberg, LLP

(57) ABSTRACT

A method of evaluating a person's olfactory perception by determining his ability to distinguish, differentiate, recognize, recall and remember distinct odors and scents when the person is presented with various odor-emitting samples. The odor-emitting samples are divided into several groups wherein the individual groups comprise two identical and one slightly different odor-emitting sample. Additionally, another group is presented to the person which comprises several individual odor-emitting samples which differ markedly from all of the other samples presented. The odor-emitting samples from the individual groups are presented to the person sequentially and the results are reported and then compared with other persons subject to the same tests. The person's olfactory perception acumen is thus recorded. This invention has great utility for many fast-growing and dynamic fields such as the food and beverage industry, academia and research facilities.

3 Claims, 1 Drawing Sheet

METHOD TO DETERMINE OLFACTORY PERCEPTION

BACKGROUND OF THE INVENTION

The present invention relates to a method of evaluating an individual person's sense of olfactory perception. More specifically, the invention concerns a method for assessing an individual's ability to differentiate between, recognize, remember, and recall different odors and scents.

An individual person's olfactory perception is generally considered to be one of the principal methods by which that person is able to make certain judgments. These judgments are important considerations which are noted and used strategically by many highly profitable and dynamic industries, such as those pertaining to perfumes and cosmetics, food preparation and supply, toxic materials such as paint and cleaning supplies, and many others. Therefore it is of great import that a method to determine which products are offensive (or pleasing) to the olfactory senses is as efficient as possible.

Olfactometers and chemosensory olfactory assays are well known. (U.S. Pat. Nos. 5,492,934 and 5,380,765). In this line of research, the general benefits of differential olfactometers (U.S. Pat. No. 4,265,248), suprathreshold odor intensity olfactometers (U.S. Pat. No. 5,457,983), physiological stimulatory models (U.S. Pat. No. 4,934,386), and even odor concentration measuring devices (U.S. Pat. No. 6,006,583) have been discovered. U.S. Pat. No. 4,563,893, discloses an apparatus for the detection of odor having a dielectric sensor.

U.S. Pat. No. 4,411,156 discloses another olfactometer in which a plurality of compartments are used by humans to "sniff" different animal litter odors. U.S. Pat. No. 5,767,385 discusses the plurality of "sniffing ports" of odoriferous sources. None of these aforementioned patents, each of which is expressly incorporated herein by reference, suggests, however, that a plurality of odoriferous sources (or samples) is grouped into a plurality of groups, each group for the purpose of gauging individual human olfactory perception. Stated another way, the aforementioned patents do not discuss a method of testing a person's olfactory perception.

The main purpose of identifying individuals with high olfactory perception is for the optimization of testing duties where accurate olfactory data is critical (e.g., the cosmetics, food, and wine industries, and in research and acadaemia).

SUMMARY OF THE INVENTION

The present invention was developed with the understanding that the sense of smell is relative, and certain testing institutions require the services of individuals who have high olfactory perception. The present invention provides a vehicle by which individuals can be "scored" on their olfactory perception.

A test person's olfactory perception is evaluated and then determined by first providing the test subject with a palette of varying odors and fragrances, and then having that person describe, in full detail, each scent sample. That person may describe his olfactory experiences in any way possible, including a description of his/her memories and feelings. This data is checked for accuracy and then recorded. Successive test takers are then given a "rank," relative to the other subjects.

That determination leads to the identification of a "super-elite" group of olfactory testers who can be joined together to produce a highly specialized team. Their main purpose would be to perform olfactory tests for any interested business, academic institution or research facility.

OBJECTS OF THE INVENTION

It is an object of the present invention to overcome the drawbacks and disadvantages of the prior art.

It is another object of the present invention to establish a method by which a person's olfactory perception may be evaluated for accuracy, recall ability, and ease of recognition.

It is another object of the present invention to establish a method that identifies a group of testers with high levels of olfactory perception, so that these testers can be utilized to conduct stringent scent tests.

It is a feature of this invention that a variety of scent samples are divided into groups which contain at least two identical samples and a third sample which differs slightly from the other two. The person being subject to the olfactory perception test would be required to identify the identical odors first, and then the third dissimilar odor. Data concerning accuracy and recognition speed is recorded for each individual. The person is then asked to describe the reasons for his/her choices. These reasons can include his/her thoughts, feelings, and memories associated with such choices. This data is also recorded. The final data is then compared with those of other test persons, whereupon the test person is "scored" with respect to his/her "olfactory ranking." This ranking system is based on the test subject's accuracy and speed in choosing the correct scents.

It is yet another object of the present invention to provide another method for identifying individuals with high olfactory perception whereby an additional, special group of samples containing markedly different scents are presented to the test subjects. This embodiment utilizes general, daily olfactory scents, and does not require the tester to distinguish between unknown products and their scents. Some examples of scents generally encountered on a daily basis include foods(tomatoes, leeks, potatoes), spices (parsley, cinnamon, pepper), and unusual products (cleaning materials, lacquer, and paint). It is also desirable that these scents be furnished in groups of ten, based on the teachings of the prior art.

The above objectives, methods and features have great utility for an interested industry preparing to unveil a new product which may emit a special odor. That special odor may be either aggressively marketed (such as perfume or food products) or downplayed (such as home cleaning supplies and paint). The methods contained herein eliminate the need for large and cumbersome testing procedures, which are often not very accurate. Also, these methods are cost and time-effective. The methods contained herein eliminate the need to test scents on hundreds of random people with minimal success. The methods here produce permanent results in that a relatively small and valuable team of people can be organized.

DETAILED DESCRIPTION OF THE PREFERRED EMBODIMENTS

Figure 1:
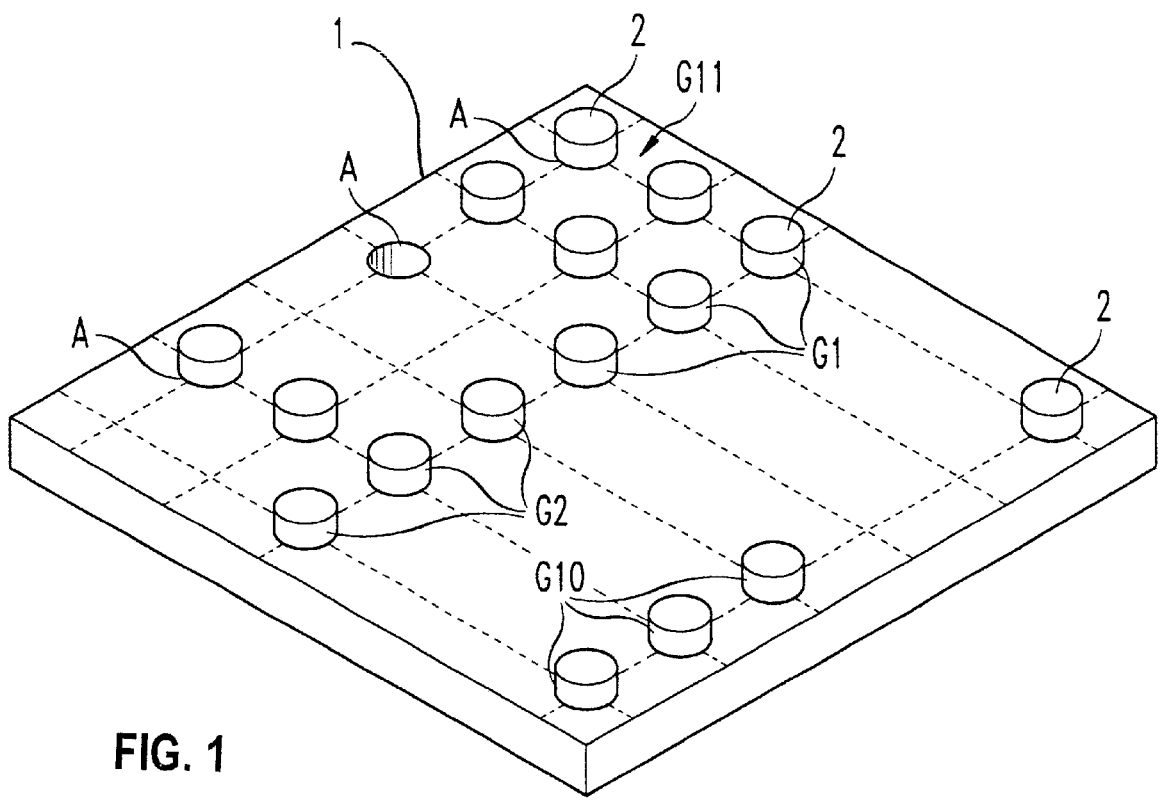
FIG. 1 is the embodiment of the present invention which illustrates the device used in the tests.

In FIG. 1, ten groups G1, G2, . . . G10 of three containers 2 each are mounted on the board 1 in the holes 7. Only G1, G2 and G10 are shown. Two containers of each group contain the same odor. The third container holds a substance having a slightly different odor than the other two. The board also contains an additional group G11 which consists of ten individual odor-emitting samples. These odors differ greatly from those in groups 1 to 10. Group G11 corresponds to "daily scents" which are characteristic of known products or procedures.

Figure 2:
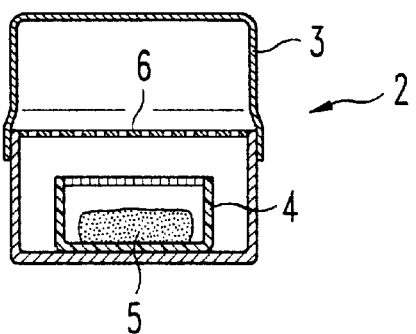
FIG. 2 is a cross-sectional view of the container used in the tests.

FIG. 2 provides a detailed illustration of a container used in the tests. The container 2 is sealed with a removable lid 3 after a filter insert 4 into which a pad 5 containing a specific odor-emitting substance has been placed. When the lid is removed, the container 2 is covered only by a "sieve" 6 which transmits odors and scents to the surrounding air, where it can be evaluated by the test persons.

The present invention is not to be considered limited in scope by the specific embodiments described above, as these embodiments are intended only to be illustrative of particular aspects of the invention. Modifications of the above-described embodiments and modes for carrying out the invention that are obvious to those skilled in the field of olfactory perception tests are intended to be within the scope of the following claims.

What is claimed is:

1. A method for determining a test person's level of olfactory perception, said method comprising:
    (a) presenting to a test person a plurality of odiferous samples, wherein said plurality of samples are divided into a plurality of groups,
    (b) evaluating reported results relating to the test person's olfactory perception with respect to each group,
    (c) comparing the test person's respective test results with those of a population of test presons,
    (d) determining the test person's relative olfactory perception based on said comparisons, and
    (e) presenting said test person with an additional group of odor-emitting samples having odors differing strongly from the odors of said plurality of groups.

2. A method according to claim 1, wherein said additional group comprises at least ten odor-emitting samples.

3. A device for determining a test person's olfactory perception, comprising in combination:
    (a) containers, each holding odor-emitting substances, and mounted on a
    (b) board having cut-outs to hold at least ten groups of three containers in each said group;
    wherein each of said containers comprise:
        (1) a removable, sealable lid,
        (2) filter inserts holding small pads saturated in odor-emitting substances, and
        (3) a sieve which allows odors to escape to the air when said lid is removed.

\* \* \* \* \*